United States Patent [19]
Kawamata et al.

[11] 3,966,918
[45] June 29, 1976

[54] METHOD OF PREPARING AQUEOUS SOLUTIONS OF STEROL GLYCOSIDES AND THEIR ESTER DERIVATIVES

[75] Inventors: Masanobu Kawamata; Hirokazu Ushimaru; Akira Sano; Yutaka Takahashi, all of Kyoto, Japan

[73] Assignee: Nippon Shinyaku Co., Ltd., Japan

[22] Filed: Nov. 22, 1974

[21] Appl. No.: 526,224

[30] Foreign Application Priority Data
Dec. 12, 1973  Japan.............................. 48-140922
Feb. 23, 1974  Japan.............................. 49-21749

[52] U.S. Cl............................. 424/182; 260/210.5
[51] Int. Cl.².................................. A61K 31/705
[58] Field of Search.................................. 424/182

[56] References Cited
UNITED STATES PATENTS
3,036,060   5/1962   Lucas et al. ......................... 424/182

OTHER PUBLICATIONS
"Detergents and Emulsifiers," 1966 Annual p. 210.
Pernarowski, M. "Remingtons Pharmaceutical Sciences," Mack Publ. Co., Easton Pa., 1965 pp. 434–440.

Primary Examiner—Lewis Gotts
Assistant Examiner—Cary Owens

[57] ABSTRACT

A method of preparing aqueous solutions of sterol glycosides and their ester derivatives characterized by solubilizing sterol glycosides and their ester derivatives by (1) dissolving said sterol glycoside or ester in a lower aliphatic alcohol and subsequently adding a hydrophilic non-ionic surface active agent, or (2) mixing or dissolving said sterol glycoside or ester with or in a lipophilic surface active agent or its solution in an organic solvent miscible with water and subsequently adding a hydrophilic surface active agent.

11 Claims, No Drawings

METHOD OF PREPARING AQUEOUS SOLUTIONS OF STEROL GLYCOSIDES AND THEIR ESTER DERIVATIVES

DETAILED DESCRIPTION OF THE INVENTION

The present invention relates to a method of preparing aqueous solutions of sterol glycosides and their ester derivatives.

Sterol glycosides or their ester derivatives, having a strong anti-inflammatory action, are very important compounds for medicines. However, owing to the poor solubilities of such compounds in water, for instance, the solubility of β-sitosteryl-β-D-glucoside is only about 7 μg/ml and that of β-sitosteryl-β-D-glucoside only about 10 μg/ml at room temperature, their applications to medical use have been seriously limited. The solubilization of such compounds has not been heretofore achieved.

According to the present invention, the sterol glycosides and esters, in order to make them useful for medicinal purposes, are formed into a homogeneous aqueous solution which is sterilizable, stable for long times and in cases when they are to be used for intravenous blood injection, intramuscular injection or subcutaneous injection, must be absorbed rapidly without any crystals separating out and also must not have harmful effects at the applied sites. But sterol glycosides and their ester derivatives are generally insoluble, or so slightly soluble in ordinary solvents used for injections, such as propylene glycol, polyethylene glycol, glycerin, ethanol etc., that crystals readily precipitate with addition of a very small amount of water. In addition, the necessary effective amount for medical use cannot be dissolved even if a large amount of a hydrophilic surface active agent is applied as only a turbid or suspended fluid is obtained.

Considering the importance of said compounds as pharmaceutical medicines, an extensive study has shown unexpectedly and surprisingly that, by using either a lower aliphatic alcohol together with a hydrophilic surace active agent or a lipophilic surface agent or its solution in an organic solvent miscrible with water together with a hydrophilic surface active agent, the solubilities of sterol glycosides and their ester derivatives can be and have been increased by 50 – 500 times or more.

The present invention thus provides a method of preparing medicinally effective aqueous solutions of sterol glycosides and their ester derivatives by solubilizing them by (1) use of a lower aliphatic alcohol together with a hydrophilic non-ionic surface active agent, or (2) by mixing or dissolving said compounds with or in a lipophilic surface active agent or its solution in an organic solvent miscible with water and subsequently adding a hydrophilic surface active agent.

A suitable lower aliphatic alcohol for use in method (1) has 1-4 carbon atoms, ethanol being preferred. As a suitable hydrophilic surface active agent, a non-ionic surface active agent having HLB of about 11-18 can be used in both methods (1) and (2) such as polyoxyethylene (hereafter abbreviated as POE), sorbitan fatty acid esters, POE fatty acid esters esters, POE ether of castor oil or hydrogenated castor oil, POE ethers of higher aliphatic, aromatic and aralkyl alcohols, as well as substances of the polyoxyalkylene series, such as copolymers of POE and polyoxypropylene. Further, fatty acid esters of water-soluble sugars and/or those of polyhydric alcohols, etc. can be also used.

As suitable organic solvents miscible with water useful in method (2), there may be used alcohols such as propylene glycol, polyethylene glycol, benzyl alcohol, ethanol or other lower alkanol, etc., amines such as triethanolamine, diethanolamine, ethylenediamine, etc., amides such as β-hydroxyethyl-lactamide, diethylacetamide, etc., and water-soluble "Cellosolves." As a suitable lipophilic surface active agent, there can be used sorbitan fatty acid esters, glycerin fatty acid esters, sucrose fatty acid esters or materials of the POE series such as POE fatty acid esters having HLB of 11 or below, POE ethers of higher aliphatic, aromatic or aralkyl alcohols, POE ethers of castor or hydrogenated castor oil, etc. Some natural materials, such as phospholipids, lecithin, etc. can also be used.

The amount of solvent and surface active agent to be used in method (1) must be somewhat varied according to the particular structure of the compound to be solubilized or said surface active agent. In general, it is preferable to dissolve the compound to be solubilized in alcohol to make a 0.2 – 10 percent solution and to add the surface active agent 40 – 60 times (in case of sterol glycosides) or 1 – 50 times (in case of ester derivatives) the weight of the compound being solubilized. The method of dissolution need not be specially restricted, but it is most preferred to dissolve the compound to be solubilized first in hot alcohol, and then adding the surface active agent to the solution, and finally completing the aqueous solution by adding water heated to 50°-80°C.

In method (2), the amounts of surface active agent and solvent also vary according to the structures of the compounds to be solubilized and the surface active agent similarly to the case (1). But generally it is preferable to use each hydrophilic and lipophilic surface active agent 20 –40 (in case of sterol glycosides) or 0.5 – 5 times (in case of ester derivatives) the weight of said compound to be solubilized and also preferably using the solvent miscible with water about 0.5 – 10 times the weight of said compound. As to the method of dissolution, the solubilized compound can be dissolved directly in the lipophilic surface active agent on heating or dissolved in the solution of the lipophilic surface active agent in the water miscible organic solvent on heating and only after the hydrophilic surface active agent or a prescribed amount of its hot concentrated aqueous solution is added to said solution and mixed can their mixtures be diluted with water heated to 50°-80°C to obtain an aqueous solution of the desired concentration.

Generally, the hot water is added under stirring, but in some cases, a homogenizer can be used instead of a stirrer. The lipophilic surface active agent is a semisolid or viscous liquid in many cases even on heating. Hence, in such cases, the lipophilic surface active agent can be dissolved, at first, in a low boiling organic solvent, such as ether, acetone, hexane, chloroform etc., then the compound to be solubilized is dissolved in the solution, and finally the solvent can be distilled away. But the above-described method, in which an organic solvent miscible with water is used, may be very advantageous industrially, because, in said method, distilling away of the solvent is unnecessary.

It is also to be understood that the surface active agent or the solvent miscible with water to be used in the present invention is not limited to individual ones but can include a mixture of such components. Moreover, a greater amount of than that described above can also be used for the solubilization of said compound. the aqueous solutions of sterol glycosides or their ester derivatives thus obtained can be diluted according to their intended use, isotonic agents added such as sodium chloride, glucose etc., and formulated for injections, or preservatives, sweetenings, aromatics etc. added for use as internal liquors. If necessary, buffer agents can be also added.

As sterol glycosides to be solubilized according to the present invention can be enumerated glucosides, lactosides and maltosides of cholesterol, β-sitosterol and stigmasterol etc., and as the ester derivatives of sterol glycosides, monoesters of cholesteryl-β-D-glucoside, β-sitosteryl-β-D-glucoside and stigmasteryl-β-D-glucoside with straight chain or branched chain, saturated or unsaturated aliphatic carboxylic acids such as acetic, propionic, butyric, isobutyric, pivalic, valeric, isovaleric, caproic, isocaproic, caprylic, capric, lauric, myristic, palmitic, oleic, arachidic acids, etc., aromatic carboxylic acids such as benzoic acid etc., aralkyl carboxylic acids such as phenyl acetic acid, and heterocyclic acids such as nicotinic acid etc. and monoesters of said glucosides with sulfonic acids such as methane sulfonic acid, toluene sulfonic acid etc., as well as tetraesters of said glucosides with aliphatic carboxylic acids of 1–10 carbon atoms such as acetic, isovaleric, caproic acids etc.

The present invention is further illustrated by the following Examples, Examples 1–10 being based on method (1), and Examples 11–20 being based on method (2).

EXAMPLE 1

In 100 ml of ethanol, 200 mg of cholesteryl-β-D-glucoside is dissolved on heating, 12 g of POE (20) sorbitan monooleate is dissolved in said solution, and then about 250 ml of water for injection of about 60°C is added to make a homogeneous solution. After being cooled, said solution is made up to 400 ml with water for injection, and stored as the stock liquor for pharmaceutical manufacturing. For instance, for the preparation of an injection, 400 ml of said stock liquor is added with about 400 ml of water for injection containing 50 g of glucose, made up to 1 liter by further addition of water for injection, filtered through a membrane filter, divided into each 5 ml portions, charged into ampoules, sterilized at 121°C for 20 minutes and used for injections.

EXAMPLE 2

In 10 ml of ethanol, 100 mg of β-stigmasteryl-β-D-lactoside is dissolved on heating and 5 g of sucrose monopalmitate is added. Then, according to Example 1, 400 ml of the stock liquor for pharmaceutical manufacturing is prepared. For instance, for the preparation of an internal liquid medicine, to 400 ml of said original are added 0.6 g of methylparaben and 0.15 g of propylparaben and dissolved on heating, and further white sugar is dissolved. Then the solution is made up to 500 ml with distilled water and is used as an internal medicine.

EXAMPLE 3

In 100 ml of ethanol, 200 mg of β-sitosteryl-β-D-glucoside is dissolved on heating and 15 g of POE (60) hydrogenated castor oil is added. Then, according to Example 1, 400 ml of the stock liquor for pharmaceutical manufacturing is prepared.

EXAMPLE 4

In 300 ml of ethanol is dissolved 1 g of β-sitosteryl-β-D-glucoside monobutylate on heating, and to said solution is added 2.5 g of POE (40) hydrogenated castor oil and according to Example 1, 400 ml of the stock liquor for pharmaceutical manufacturing is prepared.

EXAMPLE 5

In 50 ml of ethanol is dissolved 1 g of cholesteryl-β-D-glucoside monolaurate on heating, and to said solution is added 40 g of POE (20) cetyl ether, and according to Example 1, 400 ml of the stock liquor for pharmaceutical manufacturing is prepared.

EXAMPLE 6

In 50 ml of ethanol is dissolved 1 g of β-sitosteryl-β-D-glucoside monopalmitate on heating, and to said solution is added 40 g of POE (50) hydrogenated castor oil, and according to Example 1, 400 ml of the stock liquor for pharmaceutical manufacturing is prepared.

EXAMPLE 7

In 50 ml of ethanol is dissolved 1 g of stigmasteryl-β-D-glucoside monophenyl acetate on heating, and to said solution is added 40 g of POE (20) sorbitan monosterate, and according to Example 1, 400 ml of the stock liquor for pharmaceutical manufacturing is prepared.

EXAMPLE 8

In 20 ml of ethanol is dissolved 1 g of β-sitosteryl-β-D-glucoside mono-3,4,5-trimethoxybenzoate on heating, and to said solution is added 5 g of POE (60) hydrogenated castor oil, and according to Example 1, 400 ml of the stock liquor for pharmaceutical manufacturing is prepared.

EXAMPLE 9

In 50 ml of ethanol is dissolved 1 g of cholesteryl-β-D-glucoside monotoluenesulfonate, and to said solution is added 10 g of POE (25) stearate, and according to Example 1, 400 ml of the stock liquor for pharmaceutical manufacturing is prepared.

EXAMPLE 10

In 50 ml of ethanol is dissolved 1 g of β-sitosteryl-β-D-glucoside tetraacetate on heating, and to said solution is added 10 g of POE (20) sorbitan monooleate, and according to Example 1, 400 ml of the original liquor for pharmaceutical manufacturing is prepared.

EXAMPLE 11

In a mixture of 4 g of yolk lecithin and 5 ml of ethanol is dissolved 200 mg of β-sitosteryl-β-D-glucoside, and to said solution is added 20 ml of 20 w/v % aqueous solution of POE (60) hydrogenated castor oil of about 70°C under stirring to dissolve homogeneously. Said homogeneous solution is made up to 100 ml with distilled water to be made an original solution for pharmaceutical manufacturing. For instance, in case of the preparation of an injection, 100 ml of said original liquor is diluted with about 700 ml of water for injection containing 9 g of sodium chloride, diluted further with water for injection to be made up to 1 liter filtered through a membrane filter, divided into each 5 ml por-

EXAMPLE 12

In a mixture of 4 g of sorbitan monooleate and 5 ml of ethanol is dissolved 200 mg of cholesteryl-β-D-glucoside and to said solution is added 20 ml of 20 w/v % aqueous POE (20) monooleate solution of about 70°C, and according to Example 11, 100 ml of the original liquor for pharmaceutical manufacturing is prepared.

EXAMPLE 13

In a mixture of 2 g of sorbitan monooleate and 3 ml of benzyl alcohol is dissolved 1 g of β-sitosteryl-β-D-glucoside monopropionate and to said solution is added 15 ml of 20 w/v % aqueous Cremophor EL (POE, castor oil) solution of about 70°C under stirring, and according to Example 11, 100 ml of the original liquor for pharmaceutical manufacturing is prepared.

EXAMPLE 14

In a mixture of 2 g of POE (4.2) lauryl ether and 2 g of propylene glycol is dissolved 1 g of cholesteryl-β-D-glucoside monoisocaproate, and to said solution is added under stirring 15 ml of 20 w/v % aqueous POE (25) lauryl ether solution of about 70°C, and according to Example 11, 100 ml of the original liquor for pharmaceutical manufacturing is prepared.

EXAMPLE 15

In a mixture of 2.5 g of POE (10) hydrogenated castor oil and 3 ml of ethanol is dissolved 1 g of stigmasteryl-β-D-glucoside monocaprate, and to said solution is added under stirring 15 ml of 20 w/v % aqueous POE (60) hydrogenated castor oil solution of about 70°C, and according to Example 11, 100 ml of the original liquor for pharmaceutical manufacturing is prepared.

EXAMPLE 16

In a mixture of 3 g of sorbitan sesquioleate and 5 ml of ethyl ether is dissolved 1 g of cholesteryl-β-D-glucoside monolaurate and after ether is distilled away, 15 ml of 20 w/v % aqueous POE (20) monolaurate solution of about 70°C is added under stirring, and according to Example 11, 100 ml of the original liquor for pharmaceutical manufacturing is prepared.

EXAMPLE 17

In a mixture of 3 g of sorbitan monopalmitate and 5 ml of ethanol is dissolved 1 g of β-sitosteryl-β-D-glucoside monopalmitate and to said solution is added under stirring 20 ml of 20 w/v % aqueous POE (60) hydrogenated castor oil solution of about 70°C, and according to Example 11, 100 ml of the original liquor for pharmaceutical manufacturing is prepared.

EXAMPLE 18

In a mixture of 2 g of glyceryl monostearate and 3 g of propylene glycol is dissolved 1 g of β-sitosteryl-β-D-glucoside monophenyl-acetate on heating and to said solution is added under stirring 15 ml of 20 w/v % aqueous solution of POE (20) cetyl ether of about 70°C, and according to Example 11, the original liquor for pharmaceutical manufacturing is prepared.

EXAMPLE 19

In a mixture of 1 g of sucrose distearate and 2 g of macrogol 300 (PEG-300) is dissolved 1 g of stigmasteryl-β-D-glucoside mononicotinate on heating and to said solution is added under stirring 10 ml of 20 w/v % of aqueous solution of POE (25) lauryl ether of about 70°C, and according to Example 11, 100 ml of the original liquor for pharmaceutical manufacturing is prepared.

EXAMPLE 20

In a mixture of 3 g of sorbitan monostearate and 5 ml of ethanol is dissolved 1 g of β-sitosteryl-β-D-glucoside tetracaproate on heating and to said solution is added 25 ml of 20 w/v % aqueous POE (20) monooleate solution of about 70°C, and according to Example 11, 100 ml of the original liquor for pharmaceutical manufacturing is prepared.

What is claimed is:

1. A method of preparing an aqueous solution suitable for oral or injectable administration of an anti-inflammatory sterol glycoside or an ester thereof which comprises dissolving said sterol glycoside or an ester thereof in ethanol and subsequently adding to the solution polyoxyethylene hydrogenated castor oil and water.

2. A method according to claim 1 wherein the sterol glycoside or ester is selected from the group consisting of cholesteryl-β-D-glucoside, β-stigmasteryl-β-D-lactoside, β-sitosteryl-β-D-glucoside, β-sitosteryl-β-D-glucoside monobutylate, cholesteryl-β-D-glucoside monolaurate, β-sitosteryl-β-D-glucoside monopalmitate, stigmasteryl-β-D-glucoside monophenyl acetate, β-sitosteryl-β-D-glucoside mono-3,4,5-trimethoxybenzoate, cholesteryl-β-D-glucoside monotoluenesulfonate, β-sitosteryl-β-D-glucoside tetraacetate, β-sitosteryl-β-D-glucoside monopropionate, cholesteryl-β-D-glucoside monoisocaproate, stigmasteryl-β-D-glucoside monocaprate, β-sitosteryl-β-D-glucoside monophenyl-acetate, stigmasteryl-β-D-glucoside mononicotinate and β-sitosteryl-β-D-glucoside tetracaproate.

3. A method according to claim 1 wherein the sterol glycoside or ester thereof is mixed with a sorbitan fatty acid ester.

4. A method according to claim 1 wherein the polyoxyethylene hydrogenated castor oil is added as an aqueous solution.

5. A method according to claim 3 wherein the sorbitan fatty acid ester is sorbitan monopalmitate.

6. A method according to claim 3 wherein the sorbitan fatty acid ester is sorbitan monostearate.

7. A method according to claim 3 wherein the sorbitan fatty acid ester is sorbitan sequioleate.

8. A pharmaceutical composition of a sterol glycoside or an ester thereof in an aqueous solution comprising a first solution of said sterol glycoside or an ester thereof in ethanol, said first solution being in admixture with an aqueous medium and polyoxyethylene hydrogenated castor oil.

9. A pharmaceutical composition according to claim 8 wherein said aqueous medium includes an isotonic agent.

10. A pharmaceutical composition according to claim 9 wherein said isotonic agent is sodium chloride or glucose.

11. A pharmaceutical composition according to claim 8 wherein said ethanolic solution of the sterol glycoside or an ester thereof includes a sorbitan fatty acid ester.

* * * * *